United States Patent [19]

Esposito

[11] Patent Number: 4,927,073

[45] Date of Patent: May 22, 1990

[54] FOLDABLE AND STERILIZABLE COMPARTMENTALIZED ORGANIZER

[76] Inventor: Ruth Esposito, 1008 Spruce St., Philadelphia, Pa. 19107

[21] Appl. No.: 257,453

[22] Filed: Oct. 13, 1988

[51] Int. Cl.$^5$ .................. B65D 5/36; A61B 19/02
[52] U.S. Cl. .................. 229/117.07; 206/370; 206/438; 229/170.17; 229/120.31
[58] Field of Search .............. 206/438, 439, 363, 370, 206/557, 558, 562, 563, 564, 570–572; 229/41 R, 41 B, 120.16, 120.17, 120.31, 120.37, 120.38, 117.07, 117.03

[56] References Cited

U.S. PATENT DOCUMENTS

| | | | |
|---|---|---|---|
| Re. 23,597 | 12/1952 | Bergstein | 229/41 R |
| 728,749 | 5/1903 | McCord | 229/117.07 X |
| 973,068 | 10/1910 | Putnam | 229/117.07 X |
| 1,506,137 | 8/1924 | Scruby | 229/117.07 |
| 2,036,995 | 4/1936 | Bennett | 229/117.07 X |
| 2,485,028 | 10/1949 | Bauernfreund et al. | 229/41 R |
| 2,823,847 | 2/1958 | Barnes et al. | 229/41 B |
| 2,833,458 | 5/1958 | Toensmeier | 229/117.07 X |
| 2,918,206 | 12/1959 | Kleingers, Jr. | 229/41 B |
| 3,180,555 | 4/1965 | Barrett | 229/41 R |
| 3,770,119 | 11/1973 | Hultberg et al. | |
| 3,942,634 | 3/1976 | Gandi et al. | 206/210 |
| 4,168,001 | 9/1979 | Horvath et al. | 206/370 |
| 4,352,429 | 10/1982 | Newman | 206/439 |
| 4,523,679 | 6/1985 | Paikoff et al. | 206/370 |
| 4,757,937 | 7/1988 | Maio et al. | 229/117.07 |

*Primary Examiner*—Bryon P. Gehman
*Attorney, Agent, or Firm*—John F. A. Earley; John F. A. Earley, III; P. Michael Walker

[57] ABSTRACT

A foldable and sterilizable organizer for use in the operating room or at patient bedside is formed from cardboard and includes means to prevent recollapse. Side, end and transverse walls are pulled into position by a strap which then locks the walls into an upright position. Divider walls are provided to subdivide the compartments, and one compartment may include a closed top.

28 Claims, 4 Drawing Sheets

FOLDABLE AND STERILIZABLE COMPARTMENTALIZED ORGANIZER

BACKGROUND OF THE INVENTION

1. Field of the Invention

This invention relates to a sterilant package, and more particularly to a compartmentalized sterilant package in which sutures and medical supplies and instruments are organized for use in the operating room or at patient bedside.

2. Description of the Prior Art

There are many sterilant packages currently used by the medical professions. Most of these packages contain a single instrument, or the like, which has been sterilized and placed inside a package or which is sterilized while inside a package.

It is well known in the art that sterilant packages are provided consisting of an outer layer of gas barrier material and at least one sheet of gas releasing paper or the like comprising the inner package layer. A medical instrument or other item is contained inside the package. In U.S. Pat. No. 4,352,429 to Newman, a flexible, sterilizable package is provided to store and transport a single sterilized article. Numerous separate packages, each containing a single instrument or suture pack, are used during one operation.

An example of a dual compartment sterilant package is disclosed by Gandi et al in U.S. Pat. No. 3,942,634. Upon application of heat to the package, gaseous formaldehyde is released to sterilize the instruments. The user then removes the sterilized instruments from their package (or packages) at the time of use. Once removed from their packages, the instruments must be kept free from air-borne contaminants and the like.

Because it is necessary to have many sterile instruments and supplies available for each procedure, there are also available pre-sterilized kits for use in operating rooms, each kit containing the instruments and materials commonly used in a particular procedure. Use of these kits is limited by the preselection of articles placed in them. Also, the known kits are all rigid metal or plastic trays which are placed on tables or shelves in the operating room (or patient room) away from the patient and not immediately at hand for the surgeon, nurse, or other medical personnel. Examples of such kits are disclosed in U.S. Pat. No. 4,523,679 to Paikoff et al and U.S. Pat. No. 3,770,119 to Hultberg et al. These tray kits, with their enclosed instruments, are sterilized as a whole and taken into a sterile operating room before being opened. Other methods of sterilizing instruments are also well known in the art. One of these methods involves packages which include gas releasing sterilizer sheets; another method uses equipment which sterilizes by use of heat or steam. Instruments and medicaments sterilized by these methods are usually removed from their packages or the sterilizing equipment and then placed onto a sterile field until use. An advantage of the presterilized tray kits is that everything is kept at hand, but the disadvantage of the kits is that only preselected medicant packages and instruments are available. Complex surgical procedures may require 200 suture packets alone, and a multitude of tiny instruments and supplies. All such items are counted prior to surgery and before surgical wound closure. The presterilized tray kits are generally used only for simple recurrent procedures. Thus, allowances are not made for specific patient needs or surgical team preferences. Heretofore, no one has established a container that addresses this organizational need.

There are also known to be collapsible and foldable trays, most commonly used in restaurant services. Such trays are erected from previously folded and collapsed sheets of cardboard, or the like material. When erected, the food items, such as beverage containers and sandwich packages fill the compartments and prevent recollapse of the tray. Such recollapsible trays are not suitable for use in operating rooms where recollapse may not only cause spillage and contamination of instruments, but spillage or breakage of the contents, such as vials of drawn blood, may be life threatening. Heretofore, no one in the prior art has felt he could rely on a collapsible container/tray and the more expensive metal or plastic, non-disposable trays have been standard.

There is, therefore, a need for a non-rigid, foldable, sterilizable container with multiple compartments which is not already filled with preselected instruments and medications, but which is divided so that it can hold any combination of instruments preferred by an individual surgeon and staff. It is also important, where speed is essential, that a collapsible tray be quickly erected and easily locked into a rigid, non-collapsible state. For the sake of economy, and more importantly for the prevention of cross contamination between patients and medical staff, it is also preferable that an organizer for operating room use be disposable.

SUMMARY OF THE DISCLOSURE

The aforementioned prior art problems are obviated by the non-rigid foldable, sterilizable, compartmentalized organizer of this invention. A foldable, preferably cardboard, tray is compartmentalized and has self-forming means which convert the tray into an open box for use in an operating room. The organizer is sterilized, in its folded condition, in a sterilizable bag.

The folded, unconverted tray is formed by folding an elongated cardboard strip so that the two elongated sides fold towards each other over a central strip area. Transverse walls are attached to the sides and are folded flat on top of the strip central area, the sides covering both the transverse divider walls and the central area. The short ends are folded toward one another atop the sides. At the time of use, the tray is removed from the sterilizing bag and assembled.

To convert the tray to a box, a strap, which runs through all the transverse walls, is pulled toward the first short end to lift each divider to the perpendicular, simultaneously lifting the sides and ends to the perpendicular to form the side and end walls of a box with an open top. The strap engages a wall to lock the box in the erected condition. The second short end is folded against itself and inward to form an end compartment with a closed top and a self-forming diagonal brace. Additional dividers are provided to be inserted in the compartments formed by the box walls and the strap. All items placed into the sterilized container have been previously sterilized. Each nurse or doctor can choose what items to include in the tray, depending upon the operation being performed.

It is, therefore, an object of this invention to provide a foldable, sterilizable, compartmentalized organizer for use in operating rooms and at patient bedside.

It is another object of this invention to provide an organizer for medical instruments which includes individual compartments for selected supplies and suture packs.

It is yet another object of this invention to provide a compartmentalized organizer which is foldable and collapsible and which locks into the erected condition to prevent recollapse.

It is still another object of this invention to provide a compartmentalized, sterilized organizer which is disposable, to prevent cross contamination between patients and staff, and to eliminate the need for costly resterilization of trays.

These and other objects will be more readily ascertainable to one skilled in the art from a consideration of the following Figures, description and exemplary embodiments, with the understanding that the drawings are illustrative only and that changes may be made in the specific construction illustrated and described within the scope of the appended claims.

BRIEF DESCRIPTION OF THE DRAWING(S)

DETAILED DESCRIPTION OF THE PREFERRED EMBODIMENT(S)

Figure 1:
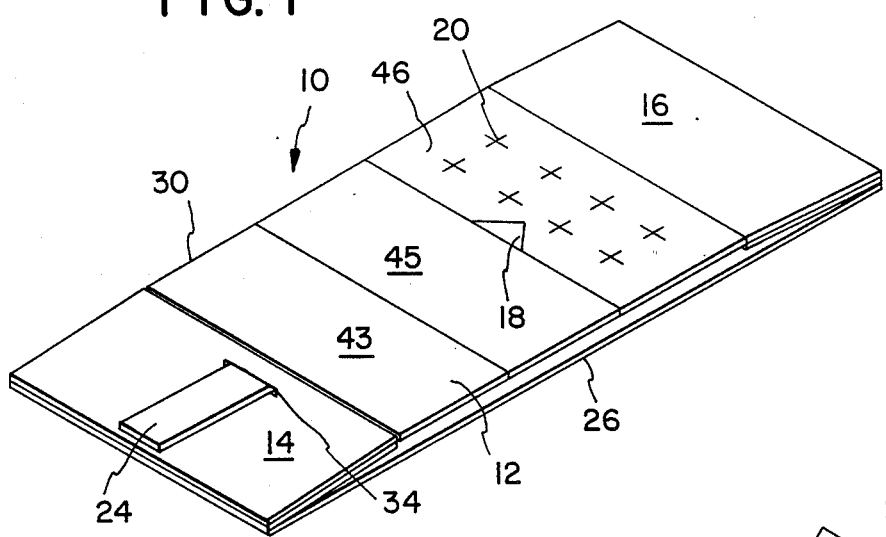
FIG. 1 is a perspective view of the organizer of this invention in the collapsed condition.
Figure 2:
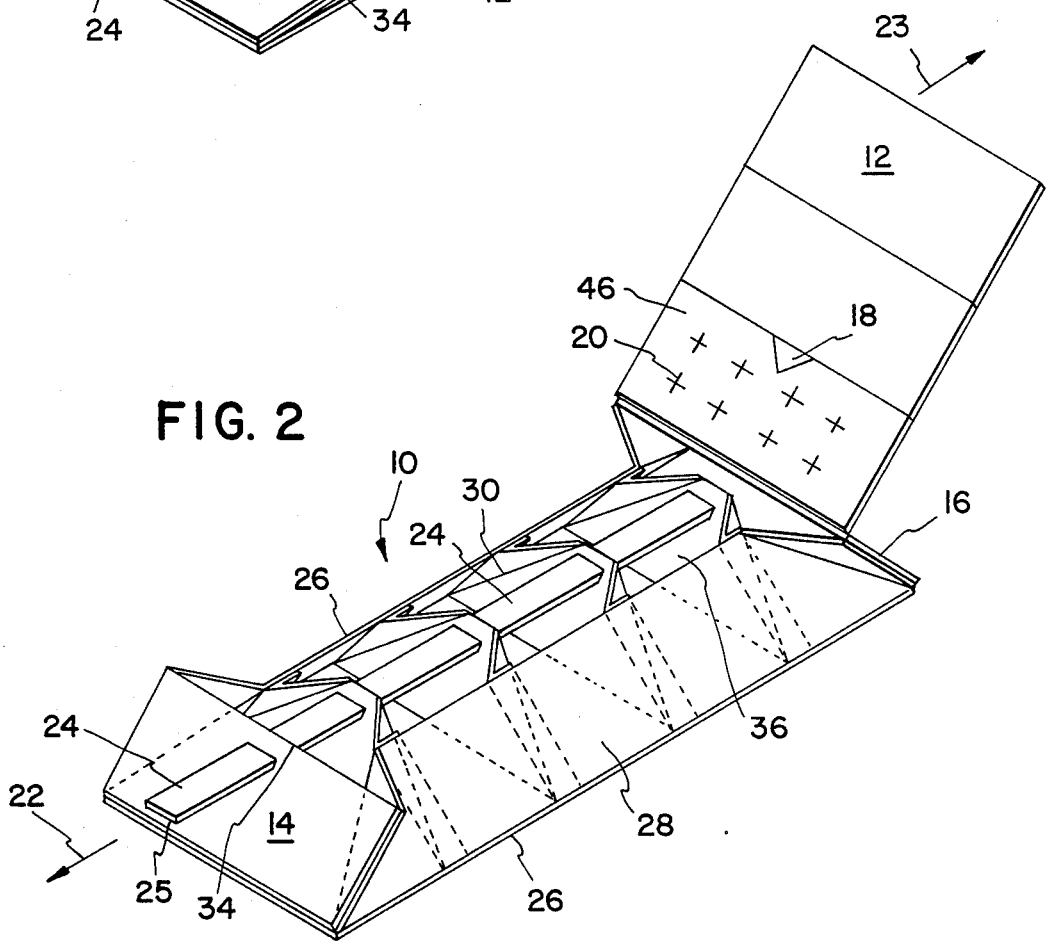
FIG. 2 is a perspective view of the organizer of this invention partially erected.

Referring now to the drawings, and more particularly to FIGS. 1 and 2, tray 10 of this invention is shown in its collapsed condition. Organizer tray 10 is formed from a single pre-cut and prefolded strip of sterilizable material, preferably cardboard. Organizer tray 10 is sterilized while in the collapsed condition, preferably in a sealed sterilizing bag of the type which releases sterilant gas when heat is applied. Preferably, organizer tray 10 is removed from its sterilant packaging in an operating room or other sterile environment. Organizer 10 is preferably formed into a tray from a single sheet of material having central area 26 which forms tray bottom 26, sides 28 and 30 which form side walls 28 and 30, end pieces 14 and 16 which form end walls 14 and 16, and transverse pieces 36 which form transverse walls 36. Strap 24, with loose end 25, extends through slots 34 in walls 36 and is attached at its other end to the wall 36 furthermost from end 14. Tongue 12 extends from end wall 16 and includes tab 18, sections 43 and 45 and perforated section 46. Perforated section 46 is better explained with reference to FIG. 6. In the collapsed condition, sides 28 and 30, with walls 36 attached, are folded towards each other over bottom 26. Ends 14 and 16 are folded inward so that unattached end of tongue 12 abuts end 14. To convert tray 10 to the erect position from the collapsed condition of FIG. 1, tongue 12 is lifted in the position of arrow 23 and strap 24 is pulled in the direction of arrow 22.

Figure 3:
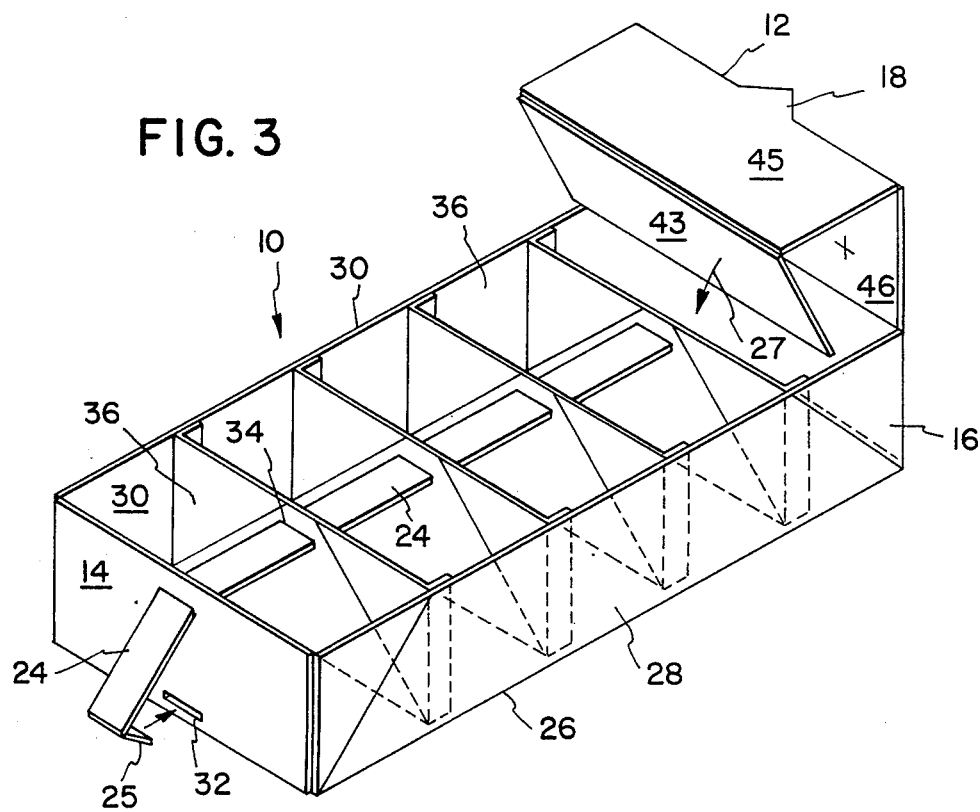
FIG. 3 is a perspective view of the organizer of this invention with the second end partially folded inward.
Figure 4:
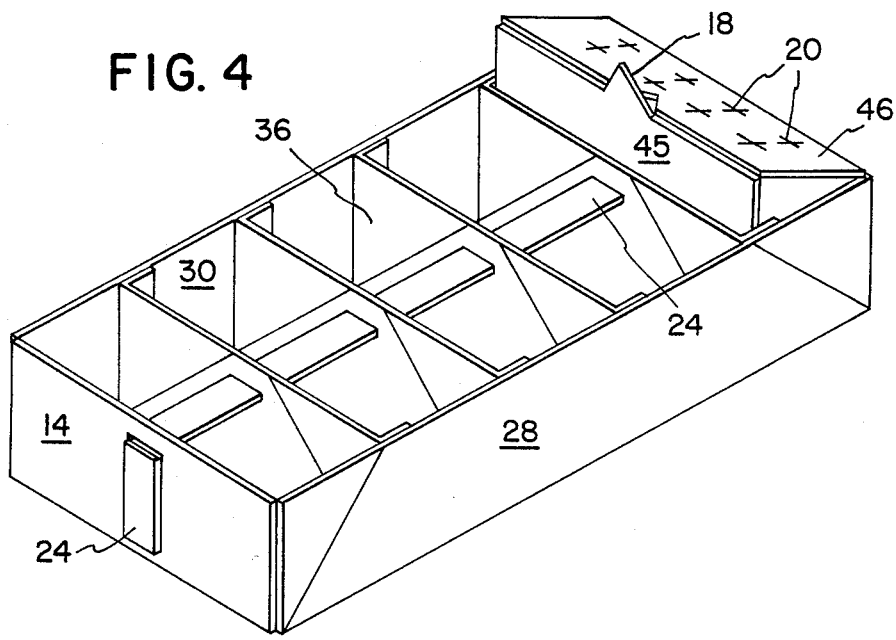
FIG. 4, is a perspective view of the organizer of this invention with the closed end compartment partially formed.

FIGS. 3 and 4 illustrate the manner in which accidental recollapse of erected organizer tray 10 is prevented. Walls, 14, 16, 28, 30, and 36 are perpendicular to tray bottom 26 and strap 24 is parallel to bottom 26. End 25 of strap 24 is inserted into slot 32 in wall 14. Tongue 12 with sections 43, 45 and 46 is folded twice inward in the direction of arrow 27, section 45 forming an upright wall, section 43 forming a diagonal brace, and section 46 forming a closed top for a compartment of tray 10. End 25 locks into place in slot 32 and strap 24 and brace 43 prevent the walls from recollapse. Tab 18 is provided to retrieve such items as may be stored in the potential space of the closed compartment formed by tongue 12.

Figure 5:
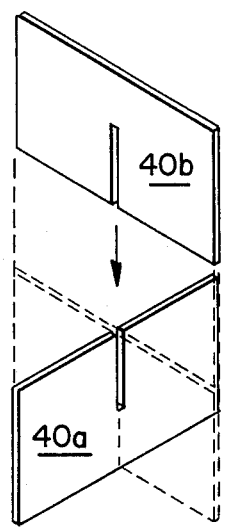
FIG. 5 is an isometric view of a divider for use in the organizer of this invention.
Figure 5:
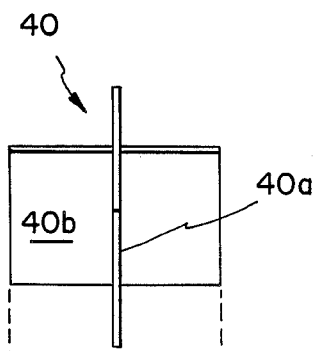
Figure 6:
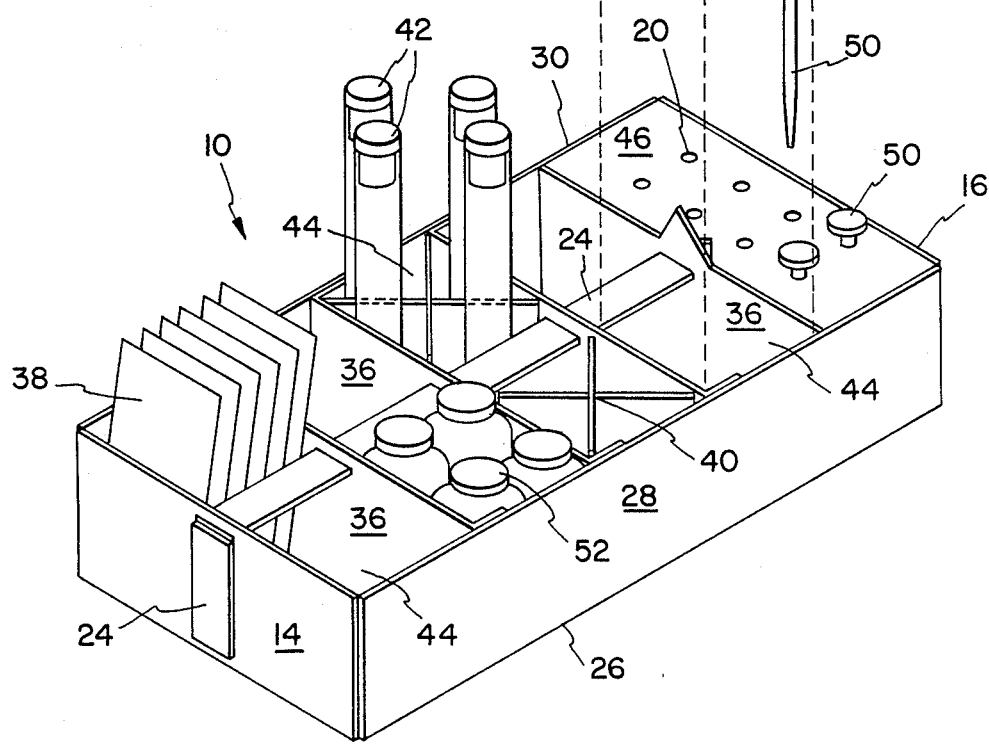
FIG. 6 is a partially exploded view of the erected and partially filled organizer of this invention.

Now referring to FIGS. 5 and 6, organizer tray 10 is illustrated in its completely erected condition and partially filled for use. Walls 14, 16, 28, 30 and 36 are perpendicular to bottom 26. Strap 24 not only holds the tray in its erected position, but serves as a divider for compartments 44. Additional dividers 40 may be placed into compartments 44. Dividers 40 are formed by assembling preformed and pre-slit interlocking pieces 40a and 40b. User preference then determines into which compartments 44 each divider 40 is placed. Dividers 40 are stored unassembled underneath sides 28 and 30 during sterilization.

In use, organizer 10 is assembled in an operating room, or at bedside. The compartments 44 are conveniently sized to retain, without danger of spillage, bandage packages 38, suture packages, or the like; test tubes or vials 42 of blood or other liquid specimens; and medicine containers 52, or the like. The closed compartment formed by tongue 12 provides accessible retainers for elongated, narrow instruments; tees 50 (used in cardiac surgery), or other elongated devices, such as thermometers. When placed at patient side or onto a sterile field, compartmentalized organizer 10 provides quick assembly and easy access to all supplies.

Figure 7:
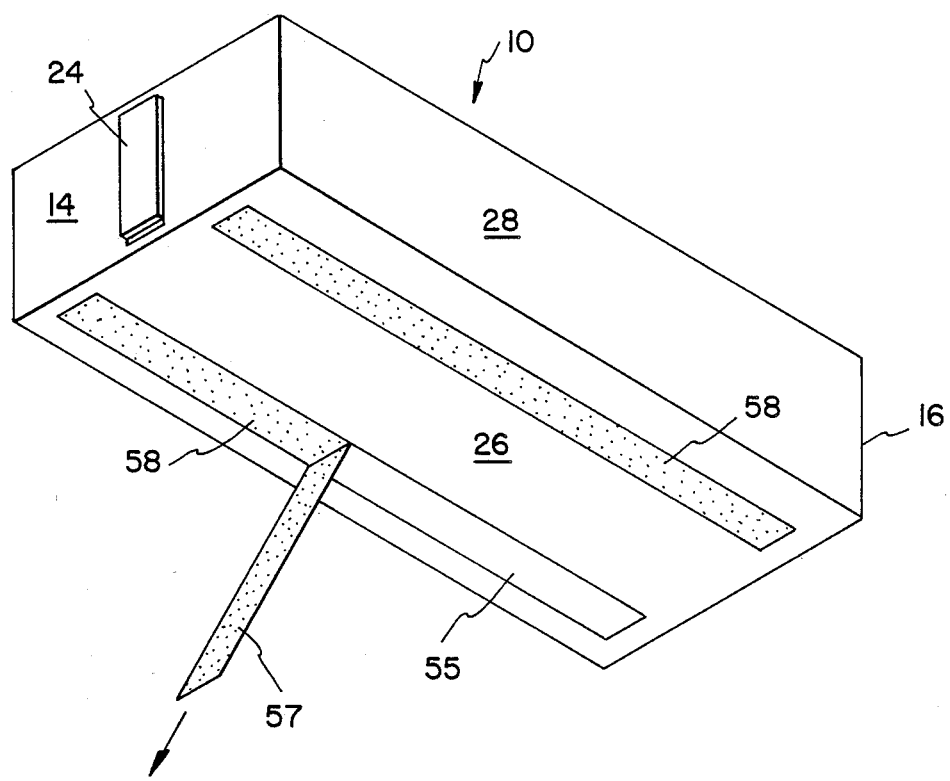
FIG. 7 is a perspective view of the underside of the tray bottom showing strips of sticking tape.

FIG. 7 illustrates assembled tray 10 with walls 14 and 28 and bottom 26. Two elongated tape strips 58 extend along the length of bottom 26. Each strip 58 is covered with cover strip 55, which is removed so that tray 10 will adhere to any surface, preventing accidental sliding.

There are several variations which can be practiced in the scope of this invention. The compartments may be subdivided by dividers 40 or they may remain undivided. It is preferred that the tray be constructed of cardboard, but any foldable, lightweight, disposable sterilizable material sheet is within the scope of this invention. The tray has been illustrated with four walls 36, but more or less walls are within the scope of this invention.

There are many advantages to the sterilizable organizer of this invention. Chiefly, it provides an inexpensive organizer for use in operating rooms. It is collapsible for economy of storage space and ease of sterilization. It is easily customized for the individual user by the addition of dividers.

Having now illustrated and described my invention, it is not intended that such description limit this invention, but rather that this invention be limited only by reasonable interpretation of the appended claims.

What is claimed is:

1. A packaged sterilant organizer comprising
   a sealed package formed of sterilizable, contamination-impermeable material, and
   a folded compartmentalized tray completely enclosed in said package and packaged in a substantially collapsed condition and having a bottom, a plurality of wall members foldably attached to the bottom, an operating strap for erecting said tray into an open box having a plurality of compartments, and means for locking said tray into the erected condition, a sterilizable, elongated semi-rigid sheet having a central area, a first side foldably attached to the central area, a second side foldably attached to the central area, a first end piece foldably attached to the central area, a second end piece foldably attached to the central area, and a tongue having a first end portion and a second end portion, the tongue first end portion being connected to the first end piece, said first and second sides being folded equidistantly over said central area, said second end piece including a strap locking means for locking the second end portion of the strap to the second end piece, said second end piece being folded inward over said first and second sides, said tongue second end portion abutting the edge of the second end piece, a plurality of transverse wall members extending across the central area between the first and second sides, each said transverse wall member including a slot, said strap extending through said slots in said transverse wall members to said second end piece and being attached to the transverse wall member furthermost from said second end piece, whereby when said strap is pulled outwardly from said second end piece, said first and second sides and said first and second end pieces are drawn perpendicular to said central area to erect side and end walls and said strap is locked to said second end piece to prevent recollapse of said tray, converting said sheet into a rigid compartmentalized tray.

2. The sterilant organizer according to claim 1, wherein said tongue, when folded inwardly into said rigid tray, forms a closed compartment, and wherein a top of said closed compartment includes apertures for receiving medical instruments.

3. A collapsible, sterilizable, compartmentalized tray for holding medical instruments and supplies for use in operating rooms and at bedside of a hospital patient, comprising a bottom wall,
a first wall connected to the bottom wall,
a second wall connected to the bottom wall,
a third wall connected to the bottom wall,
a transverse wall extending across the bottom wall,
erecting and compartment forming means for erecting the first, second, and third walls in an erected condition and for forming a plurality of compartments, and
locking means for locking the first, second, and third walls in an erected condition,
said erecting and compartment forming means including
an operating strap having a first end portion and a second end portion,
the operating strap being connected to the second wall at the operating strap first end portion and being extendable over the bottom wall to the third wall forming a tray partition,
said transverse wall having a slot through which the operating strap extends so that when the operating strap second end portion is pulled towards the third wall the transverse wall is drawn perpendicular to the bottom wall in an erected condition,
said locking means including
attachment means for attaching the second end portion of the operating strap to the third wall.

4. The tray of claim 3, further including
insertable divider walls insertable into the compartments for creating additional compartments.

5. The tray of claim 4, further including a closed compartment formed in the tray, said closed compartment having a top portion having apertures for receiving medical instruments.

6. The tray of claim 5, said locking means being integral with the tray.

7. The tray of claim 6, further including a strip of tape mounted on the outside of the bottom wall, said tape having an adhesive side facing outwardly to anchor said tray to a sterile field.

8. The tray of claim 6, further including
a cover strip on each strip of tape.

9. The tray of claim 8, further including
a package formed of sterilizable, contamination-impermeable material for holding the tray until it is desired to erect the tray.

10. The tray of claim 3, said locking means being integral with the tray.

11. The tray of claim 3, further including
a closed compartment formed in the tray, said closed compartment having a top portion having apertures for receiving medical instruments.

12. The tray of claim 3, further including
a strip of tape mounted on the outside of the bottom wall, said tape having an adhesive side facing outwardly to anchor said tray to a sterilizable field.

13. The tray of claim 12, further including
a cover strip on each strip of tape.

14. The tray of claim 3, further including
a package formed of sterilizable, contamination-impermeable material for holding the tray until it is desired to erect the tray.

15. A collapsible, sterilizable, compartmentalized tray for holding medical instruments and supplies for use in operating rooms and at bedside of a hospital patient, comprising a bottom wall,
a first wall connected to the bottom wall and having a top end portion,
a second wall connected to the bottom wall and having a top end portion,
a third wall connected to the bottom wall and having a top end portion,
erecting and compartment forming means for erecting the first, second, and third walls in an erected condition and for forming a plurality of compartments, and
locking means for locking the first, second, and third walls in an erected condition,
said erecting and compartment forming means including
an operating strap having a first end portion and a second end portion,
the operating strap being connected to the second wall at the operating strap first end portion and being extendable over the bottom wall to the third wall forming a tray partition,
the operating strap when pulled over the bottom wall to the third wall to erect the first, second, and third walls in an erected condition being no higher than the top end portions of the first, second, and third walls, said locking means including attachment means for attaching the second end portion of the operating strap to the third wall.

16. The tray of claim 15, further including insertable divider walls insertable into the compartments for creating additional compartments.

17. The tray of claim 15, further including a transverse wall extending across the bottom wall, the transverse wall having a slot through which the operating strap extends so that when the operating strap second end portion is pulled towards the third wall the transverse wall is drawn perpendicular to the bottom wall in an erected condition.

18. The tray of claim 17, further including insertable divider walls insertable into compartments for creating additional compartments.

19. The tray of claim 18, further including a closed compartment formed in the tray, said closed compartment having a top portion having apertures for receiving medical instruments.

20. The tray of claim 19, said locking means being integral with the tray.

21. The tray of claim 20, further including a strip of tape mounted on the outside of the bottom wall, said tape having an adhesive side facing outwardly to anchor said tray to a sterile field.

22. The tray of claim 21, further including a cover strip on each strip of tape.

23. The tray of claim 22, further including a package formed of sterilizable, contamination-impermeable material for holding the tray until it is desired to erect the tray.

24. The tray of claim 15, said locking means being integral with the tray.

25. The tray of claim 15, further including a closed compartment formed in the tray, said closed compartment having a top portion having apertures for receiving medical instruments.

26. The tray of claim 15, further including a strip of tape mounted on the outside of the bottom wall, said tape having an adhesive side facing outwardly to anchor said tray to a sterile field.

27. The tray of claim 26, further including a cover strip on each strip of tape.

28. The tray of claim 15, further including a package formed of sterilizable, contamination-impermeable material for holding the tray until it is desired to erect the tray.

* * * * *